US006589737B1

(12) United States Patent
Gruber et al.

(10) Patent No.: US 6,589,737 B1
(45) Date of Patent: Jul. 8, 2003

(54) COMPOSITIONS AND METHODS FOR LABELING OF NUCLEIC ACID MOLECULES

(75) Inventors: Christian E. Gruber, Frederick, MD (US); Po-Jen Shih, Columbia, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/574,111

(22) Filed: May 19, 2000

Related U.S. Application Data

(60) Provisional application No. 60/135,425, filed on May 21, 1999.

(51) Int. Cl.[7] .......................... C12Q 1/68; C12P 19/34; C07H 21/00
(52) U.S. Cl. .................. 435/6; 435/91.1; 435/91.2; 536/25.3
(58) Field of Search ................. 435/6, 91.1, 91.2; 536/25.3

(56) References Cited

U.S. PATENT DOCUMENTS

| | | | |
|---|---|---|---|
| 4,663,290 A | 5/1987 | Weis et al. ................. | 435/253 |
| 4,683,195 A | 7/1987 | Mullis et al. ................ | 435/6 |
| 4,683,202 A | 7/1987 | Mullis ....................... | 435/91 |
| 4,828,979 A | 5/1989 | Klevan et al. ............... | 435/6 |
| 4,683,202 A | 11/1990 | Mullis ....................... | 435/91 |
| 5,137,814 A | 8/1992 | Rashtchian et al. .......... | 435/91 |
| 5,229,283 A | 7/1993 | Berninger ................ | 435/172.3 |
| 5,244,797 A | 9/1993 | Kotewicz et al. ........... | 435/194 |
| 5,405,776 A | 4/1995 | Kotewicz et al. ...... | 435/252.33 |
| 5,409,818 A | 4/1995 | Davey et al. ............. | 435/91.21 |
| 5,436,149 A | 7/1995 | Barnes ...................... | 435/194 |
| 5,436,327 A | 7/1995 | Southern et al. .......... | 536/25.34 |
| 5,445,934 A | 8/1995 | Fodor et al. ................ | 435/6 |
| 5,455,166 A | 10/1995 | Walker ..................... | 435/91.2 |
| 5,508,166 A | 4/1996 | Tanno et al. ................. | 435/6 |
| 5,512,431 A | 4/1996 | Loeb et al. .................. | 435/5 |
| 5,512,462 A | 4/1996 | Cheng ...................... | 435/91.2 |
| 5,668,005 A | 9/1997 | Kotewicz et al. ........... | 435/194 |
| 5,700,637 A | 12/1997 | Southern .................... | 435/6 |
| 5,744,305 A | 4/1998 | Fodor et al. ................. | 435/6 |
| 5,244,797 A | 8/1998 | Kotewicz et al. ........... | 435/194 |
| 5,800,992 A | 9/1998 | Fodor et al. ................. | 435/6 |
| 5,807,522 A | 9/1998 | Brown et al. ............... | 422/50 |
| 5,837,832 A | 11/1998 | Chee et al. ................. | 436/22.1 |
| 5,912,155 A | 6/1999 | Chatterjee et al. .......... | 435/194 |
| 5,939,301 A | 8/1999 | Hughes, Jr. et al. ........ | 435/194 |
| 5,948,614 A | 9/1999 | Chatterjee .................. | 435/6 |
| 5,994,076 A | 11/1999 | Chenchik et al. ............ | 435/6 |
| 6,015,668 A | 1/2000 | Hughes et al. .............. | 435/6 |
| 6,046,038 A * | 4/2000 | Nilsen ....................... | 435/91.1 |
| 6,063,608 A | 5/2000 | Kotewicz et al. ........... | 435/194 |

FOREIGN PATENT DOCUMENTS

| | | |
|---|---|---|
| EP | 0 329 822 B1 | 8/1989 |
| EP | 0 684 315 A1 | 11/1995 |
| WO | WO 92/06188 | 4/1992 |
| WO | WO 92/06200 | 4/1992 |
| WO | WO 92/22649 | 12/1992 |
| WO | WO 96/10640 | 4/1996 |
| WO | WO 98/06736 | 2/1998 |
| WO | WO 98/08981 | 3/1998 |
| WO | WO 98/47912 | * 10/1998 |

OTHER PUBLICATIONS

Stratagene Catalog p. 39, 1988.*
Co–Pending Non–Provisional U.S. patent application Ser. No. 09/808,124, Potter et al., filed Mar. 15, 2001.
Co–Pending Non–Provisional U.S. patent application Ser. No. 09/845,157, Smith et al., filed May 1, 2001.
Supplementary European Search Report for European Patent Application No. EP 00 93 2596, completed Jul. 24, 2002.
Marton, M.J., et al., "Drug target validation and identification of secondary drug target effects using DNA microarrays," *Nat. Med.* 4:1293–1301, Nature Publishing Co. (Nov. 1998).
Schena, M., et al., "Quantitative Monitoring of Gene Expression Patterns with a Complementary DNA Microarray," *Science* 270:467–470, American Association for the Advancement of Science (1995).
Aleksandrova, L.A. et al., "Nucleoside 5'–Triphosphate Fluorescent Analogs in Nonradioactive Method for Study of Nucleic Acids," pp. 886–893, translated from *Molekulyarnaya Biologiya* 24:1100–1108 (1990). Copyright 1991 Plenum Publishing Corporation.
Aldous, W.K., and Grabill, N.R., "A Fluorescent Method for Detection of Telomerase Activity," *Diagn. Mol. Pathol.* 6:102–110 (1997).
Alexander, F. et al., "Proteolytic Processing of Avian Sarcoma and Leukosis Viruses pol–endo Recombinant Proteins Reveals Another pol Gene Domain," *J. Virol.* 61:534–542 (1987).
Alexandrova, L.A. et al., "Fluorescent Analogues of Nucleoside 5'–Triphosphates for Investigating Nucleic Acids by Nonradioactive Methods," *Molekulyarnaya Biologiya* 24:1100–1108 (1990).
Anderson, D. et al., "Rapid Generation of Recombinant Baculovirus and Expression of Foreign Genes Using the Bac–to–Bac™ Baculovirus Expression System," *Focus* 17:53–58 (1995).

(List continued on next page.)

*Primary Examiner*—Jezia Riley
(74) *Attorney, Agent, or Firm*—Sterne, Kessler, Goldstein & Fox P.L.L.C.

(57) ABSTRACT

The present invention is generally related to compositions, kits and methods for labeling nucleic acid molecules using reverse transcriptases, preferably multi-subunit reverse transcriptases such as ASLV reverse transcriptases. Specifically, the invention relates to methods, kits and compositions for fluorescently labeling nucleic acid molecules during nucleic acid synthesis. The labeled nucleic acid molecules produced in accordance with the invention are particularly suited as labeled probes for nucleic acid detection and diagnostics.

63 Claims, No Drawings

OTHER PUBLICATIONS

Barnes, W.M., "The fidelity of Taq polymerase catalyzing PCR is improved by an N–terminal deletion," *Gene* 112:29–35 (1992).

Bauer, G.J., "RNA sequencing using fluorescent–labeled dideoxynucleotides and automated fluorescence detection," *Nucl. Acids Res.* 18:879–884 (1990).

Brooks, E.M., et al., "Secondary Structure in the 3' UTR of EGF and the Choice of Reverse Transcriptases Affect the Detection of Message Diversity by RT–PCR," *BioTechniques* 19:806–815 (1995).

Canard, B. and Sarfati, R.S., "DNA polymerase fluorescent substrates with reversible 3'–tags," *Gene* 148:1–6 (1994).

Chang, H., "In situ transcription with Tth DNA polymerase and fluorescent nucleotides," *J. Immunol. Methods* 176:235–243 (1994).

Chavan, S.J. and Prochaska, H.J., "Fluorometric Measurement of Reverse Transcriptase Activity with 4',6–Diamidino–2–phenylindole," *Anal. Biochem.* 225:54–59 (1995).

Chernov, A.P., et al., "Recombinant reverse transcriptase of Rous sarcoma virus: characterization of DNA polymerase and RNAase H activities," *Biomedical Science* 2:49–53 (1991).

D'yachenko, L.B., et al., "5–Modified ddUTP Derivatives as Terminating Substrates for Reverse Transcriptases. Phosphodiesterase Hydrolysis of Oligonucleotides Terminated by These Derivatives," *Molecular Biology* 28:67–74 (1994).

Delahunty, M.D. et al., "Studies on Primer Binding of HIV–1 Reverse Transcriptase Using a Fluorescent Probe," *J. Mol. Biol.* 236:469–479 (1994).

DeRisi, J.L. et al., "Exploring the Metabolic and Genetic Control of Gene Expression on a Genomic Scale," *Science* 278:680–686 (1997).

DeStefano, J.J. et al., "Quantitative analysis of RNA cleavage during RNA–directed DNA synthesis by human immunodeficiency and avian myeloblastosis virus reverse transcriptases," *Nucl. Acids Res.* 22:3793–3800 (1994).

Divita, G. et al., "Kinetics of Interaction of HIV Reverse Transcriptase with Primer/Template," *Biochemistry* 32:7966–7971 (1993).

Flaman, J.–M. et al., "A rapid PCR fidelity assay," *Nucl. Acids Res.* 22:3259–3260 (1994).

Gebinoga, M. and Oehlenschläger, F., "Comparison of self-sustained sequence–replication reaction systems," *Eur. J. Biochem.* 235:256–261 (1996).

Gerard, G.F. et al., "cDNA Synthesis by Moloney Murine Leukemia Virus RNase H–Minus Reverse Transcriptase Possessing Full DNA Polymerase Activity," *Focus* 14:91–93 (1992).

Goodman, M.F. et al., "Nucleotide Insertion and Primer Extension at Abasic Template Sites in Different Sequence Contexts," *Ann. N.Y. Acad. Sci.* 726:132–143 (1994).

Grandgenett, D.P. et al., "A Single Subunit from Avian Myeloblastosis Virus with Both RNA–Directed DNA Polymerase and Ribonuclease H Activity," *Proc. Natl. Acad. Sci. USA* 70:230–234 (1973).

Hizi, A. and Joklik, W.K. "RNA–dependent DNA Polymerase of Avian Sarcoma Virus B77," *J. Biol. Chem.* 252:2281–2289 (1977).

Hostomsky, Z. et al., "Reverse Transcriptase of Human Immunodeficiency Virus Type 1: Functionality of Subunits of the Heterodimer in DNA Synthesis," *J. Virol.* 66:3179–3182 (1992).

Karamohamed, S. et al., "Bioluminometric Method for Real–Time Detection of Reverse Transcriptase Activity," *BioTechniques* 24:302–306 (Feb. 1998).

Karet, F.E. et al., "Quantification of mRNA in Human Tissue Using Fluorescent Nested Reverse–Transcriptase Polymerase Chain Reaction," *Anal. Biochem.* 220:384–390 (1994).

Kotewicz, M.L. et al., "Isolation of cloned Moloney murine leukemia virus reverse transcriptase lacking ribonuclease H activity," *Nucl. Acids Res.* 16:265–277 (1988).

Kvasyuk, E.I. et al., "Synthesis of 3'–fluoro–2',3'–dideoxyadenosine and –guanosine, their 5'–triphosphates, and study of substrate properties of fluorodeoxy analogues of natural 2'–deoxynucleoside 5'–triphosphates for DNA polymerases," *Bioorg. Khim.* 15:781–795 (1989).

Lawyer, F.C. et al., "High–level Expression, Purification, and Enzymatic Characterization of Full–length *Thermus aquaticus* DNA Polymerase and a Truncated Form Deficient in 5' to 3' Exonuclease Activity," *PCR Methods and Applications* 2:275–287 (1993).

Le Grice, S.F.J. et al., "Subunit–selective mutagenesis indicates minimal polymerase activity in heterodimer–associated p51 HIV–1 reverse transcriptase," *EMBO J.* 10:3905–3911 (1991).

Le Grice, S.F.J., "Human Immunodeficiency Virus Reverse Transcriptase," in *Reverse Transcriptase,* Skalka, A.M. and Goff, S.P., eds., Cold Spring Harbor Laboratory Press, Cold Spring Harbor, NY (1993), pp. 163–191.

Lokhova, I.A., et al., "5'–Derivatives of oligonucleotides as primers of DNA polymerization catalyzed by AMV reverse transcriptase and Klenow fragment of DNA polymerase 1," *FEBS Lett.* 281:111–113 (1991).

Müller, B. et al., "Interaction of Fluorescently Labeled Dideoxynucleotides with HIV–1 Reverse Transcriptase," *Biochemistry* 30:3709–3715 (1991).

Muratori, L. et al., "Quantification of Hepatitis C Virus–Infected Peripheral Blood Mononuclear Cells by In Situ Reverse Transcriptase–Polymerase Chain Reaction," *Blood* 88:2768–2774 (1996).

Ohyashiki, J.H. et al., "Non–radioisotopic and Semi–quantitative Procedure for Terminal Repeat Amplification Protocol," *Jpn. J. Cancer Res.* 87:329–331 (1996).

Prasad, V.R., "Genetic Analysis of Retroviral Reverse Transcriptase Structure and Function," in *Reverse Transcriptase,* Skalka, A.M. and Goff, S.P., eds., Cold Spring Harbor Laboratory Press, Cold Spring Harbor, NY (1993), pp. 135–162.

Rochelle, P.A. et al., "An Assay Combining Cell Culture with Reverse Transcriptase PCR To Detect and Determine the Infectivity of Waterborne *Cryptosporidium parvum,*" *Appl. Environ. Microbiol.* 63:2029–2037 (1997).

Rozovskaya, T.A. et al., "Human Immunodeficiency Virus Reverse Transcriptase: Isolation and Substrate Specificity," *Molecular Biology* 27:376–383 (1993).

Sano, K. et al., "Comparable sensitivities for detection of HIV–1 reverse transcriptase (RT) and other polymerases by RT assays requiring no radioisotopic materials," *J. Virol. Methods* 53:235–244 (1995).

Skalka, A.M., "Endonuclease Activity Associated with Reverse Transcriptase of Avian Sarcoma–leukosis Viruses," in *Reverse Transcriptase,* Skalka, A.M. and Goff, S.P., eds., Cold Spring Harbor Laboratory Press, Cold Spring Harbor, NY (1993), pp. 193–204.

Soltis, D.A. and Skalka, A.M., "The α and β chains of avian retrovirus reverse transcriptase independently expressed in *Escherichia coli:* Characterization of enzymatic activities," *Proc. Natl. Acad. Sci. USA 85:*3372–3376 (1988).

Sudiro, T.M. et al., "Rapid Diagnosis of Dengue Viremia by Reverse Transcriptase–Polymerase Chain Reaction Using 3'–Noncoding Region Universal Primers," *Am. J. Trop. Med. Hyg. 56:*424–429 (1997).

Suzuki, K. et al., "Colorimetric reverse transcriptase assay for HIV–1," *J. Virol. Methods 41:*21–28 (1993).

Suzuki, K. et al., "Poly A–linked colorimetric microtiter plate assay for HIV reverse transcriptase," *J. Virol. Methods 44:*189–198 (1993).

Suzuki, K. et al., "Detection of human immunodeficiency virus (HIV) by colorimetric assay for reverse transcriptase activity on magnetic beads," *Biotechnol. Appl. Biochem. 18:*37–44 (1993).

Takagi, M. et al., "Detection of contamination of vaccines with the reticuloendotheliosis virus by reverse transcriptase polymerase chain reaction (RT–PCR)," *Virus Res. 40:*113–121 (1996).

Thrall, S.H. et al., "Evaluation of Human Immunodeficiency Virus Type 1 Reverse Transcriptase Primer tRNA Binding by Fluorescence Spectroscopy: Specificity and Comparison to Primer/Template Binding," *Biochemistry 35:*4609–4618 (1996).

Voss, H. et al., "Automated Cycle Sequencing with Taquenase™: Protocols for Internal Labeling, Dye Primer and 'Doublex' Simultaneous Sequencing," *BioTechniques 23:*312–318 (1997).

Wiemann, S. et al., "Primer Design for Automated DNA Sequencing Utilizing T7 DNA Polymerase and Internal Labeling with Fluorescein–15–dATP," *BioTechniques 18:*688–697 (1995).

Yoshikawa, Y. et al., "Differential Display with Carboxy–X–rhodamine–Labeled Primers and the Selection of Differentially Amplified cDNA Fragments without Cloning," *Anal. Biochem. 256:*82–91 (Feb. 1998).

English language abstract of Alexandrova, L.A. et al., "Fluorescent Analogues of Nucleoside 5'–Triphosphates for Investigating Nucleic Acids by Nonradioactive Methods," *Molekulyarnaya Biologiya 24:*1100–1108 (1990) (Document AT1), Database BIOSIS, US National Library of Medicine, Accession No. 1991:113746.

International Search Report for International Application No. PCT/US00/13744, mailed Aug. 24, 2000.

* cited by examiner

COMPOSITIONS AND METHODS FOR LABELING OF NUCLEIC ACID MOLECULES

CROSS REFERENCE TO RELATED APPLICATION

This claims the benefit of provisional application No. 60/135,425 filed May 21, 1999, abandoned.

FIELD OF THE INVENTION

The present invention is in the fields of molecular and cellular biology. The invention generally relates to the use of reverse transcriptase (RT) enzymes and particularly to methods for the reverse transcription of nucleic acid molecules, especially messenger RNA molecules, to synthesize labeled (e.g. fluorescently labeled) nucleic acid molecules. The invention also relates to nucleic acid molecules produced by these methods and to the use of such labeled nucleic acid molecules as detection probes. The invention also concerns kits and compositions for making such labeled nucleic acid molecules.

BACKGROUND OF THE INVENTION cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using the enzyme reverse transcriptase (RT), which results in the production of single-stranded cDNA molecules. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a plasmid or viral vector, which is then introduced into a host bacterial, yeast, animal or plant cell. The host cells are then grown in culture media, resulting in a population of host cells containing (or in many cases, expressing) the gene of interest.

This entire process, from isolation of mRNA to insertion of the cDNA into a plasmid or vector to growth of host cell populations containing the isolated gene, is termed "cDNA cloning." If cDNAs are prepared from a number of different mRNAs, the resulting set of cDNAs is called a "cDNA library," an appropriate term since the set of cDNAs represents a "population" of genes comprising the functional genetic information present in the source cell, tissue or organism. Genotypic analysis of these cDNA libraries can yield much information on the structure and function of the organisms from which they were derived.

Retroviral Reverse Transcriptase Enzymes

Three prototypical forms of retroviral RT have been studied thoroughly. Moloney Murine Leukemia Virus (M-MLV) RT contains a single subunit of 78 kDa with RNA-dependent DNA polymerase and RNase H activity. This enzyme has been cloned and expressed in a fully active form in *E.coli* (reviewed in Prasad, V. R., *Reverse Transcriptase*, Cold Spring Harbor, N.Y.: Cold Spring Harbor Laboratory Press, p.135 (1993)). Human Immunodeficiency Virus (HIV) RT is a heterodimer of p66 and p51 subunits in which the smaller subunit is derived from the larger by proteolytic cleavage. The p66 subunit has both a RNA-dependent DNA polymerase and an RNase H domain, while the p51 subunit has only a DNA polymerase domain. Active HIV p66/p51 RT has been cloned and expressed successfully in a number of expression hosts, including *E.coli* (reviewed in Le Grice, S. F. J., *Reverse Transcriptase*, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., *EMBO Journal* 10:3905 (1991); Hostomsky, Z., et al., *J Virol.* 66:3179 (1992)). Avian Sarcoma-Leukosis Virus (ASLV) RT, which includes but is not limited to Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT, is also a heterodimer of two subunits, α approximately 62 kDa) and β (approximately 94 kDa), in which α is derived from β by proteolytic cleavage (reviewed in Prasad, V. R., *Reverse Transcriptase*, Cold Spring Harbor, N.Y.: Cold Spring Harbor Laboratory Press (1993), p. 135). ASLV RT can exist in two additional catalytically active structural forms, ββ and α (Hizi, A. and Joklik, W. K., *J. Biol. Chem.* 252: 2281 (1977)). Sedimentation analysis suggests αβ and ββ are dimers and that the α form exists in an equilibrium between monomeric and dimeric forms (Grandgenett, D. P., et al., *Proc. Nat. Acad. Sci. USA* 70: 230 (1973); Hizi, A. and Joklik, W. K., *J. Biol. Chem.* 252: 2281 (1977); and Soltis, D. A. and Skalka, A. M., *Proc. Nat. Acad. Sci. USA* 85: 3372 (1988)). The ASLV αβ and ββ RTs are the only known examples of retroviral RT that include three different activities in the same protein complex: DNA polymerase, RNase H, and DNA endonuclease (integrase) activities (reviewed in Skalka, A. M., *Reverse Transcriptase*, Cold Spring Harbor, N.Y.: Cold Spring Harbor Laboratory Press (1993), p. 193). The α form lacks the integrase domain and activity.

Various forms of the individual subunits of ASLV RT have been cloned and expressed. These include a 98-kDa precursor polypeptide that is normally processed proteolytically to β α, and a 4-kDa polypeptide removed from the β carboxy end (Alexander, F., et al., *J. Virol.* 61: 534 (1987) and Anderson, D. et al., *Focus* 17:53 (1995)), and the mature β subunit (Weis, J. H. and Salstrom, J. S., U.S. Pat. No. 4,663,290 (1987); and Soltis, D. A. and Skalka, A. M., *Proc. Nat. Acad. Sci. USA* 85:3372 (1988)). Heterodimeric RSV αβ RT has also been purified from *E. coli* cells expressing a cloned RSV β gene (Chernov, A. P., et al., *Biomed. Sci.* 2:49 (1991)). See also published PCT application WO 98/47912.

Labeling Nucleic Acid Molecules

As noted above, the conversion of mRNA to cDNA by RT-mediated reverse transcription is an essential step in the study of proteins expressed from cloned genes. Reverse transcription of nucleic acid molecules, particularly mRNA, to make labeled nucleic acid molecules (e.g., labeled cDNA) is also important in the generation of labeled probes for use in detection and diagnostics. Typically, fluorescent labels are used in the generation of such probes. To date, SuperScript™ II (an RNase H minus derivative of MMLV RT available from Life Technologies, Inc.) has been used in the generation of fluorescently labeled probes from mRNA templates (DeRisi et al., *Science* 278:680–686 (1997)). However, the incorporation rate of fluorescent nucleotides during synthesis is relatively low (less than 2%), perhaps due to the inability of MMLV RT to effectively use fluorescently labeled nucleotides as substrates during nucleic acid synthesis. Accordingly, there exists a need for more efficient incorporation of labeled nucleotides, particularly fluorescently labeled nucleotides, during reverse transcription of a nucleic acid template. Efficient incorporation of such nucleotides will allow for improved synthesis of labeled probes which may be used in the research market as well as in the field of diagnostics.

SUMMARY OF THE INVENTION

The present invention provides reverse transcriptase enzymes, compositions and kits comprising such enzymes, and methods useful in overcoming the above-described nucleic acid labeling limitations. In general, the invention relates to the use of multi-subunit RTs (particularly heterodimers and more specifically two subunit enzymes (e.g., dimers) such as HIV RT and ASLV RTs) to label synthesized nucleic acid molecules. Preferably, such labeling involves the use of labeled nucleotides, particularly fluorescently labeled nucleotides and one or more nucleic acid templates (preferably RNA and most preferably mRNA). In accordance with the invention, one or more labeled nucleic acid molecules are synthesized which are complementary to all or a portion of the one or more templates. The labeled nucleic acid molecules preferably have one or more labeled nucleotides incorporated into the synthesized molecule and in a preferred aspect, the labels are one or more fluorescent labels (which may be the same or different).

The invention also relates to compositions for use in the invention and such compositions may comprise one or more multi-subunit RTs (particularly HIV and ASLV RTs). Such compositions may further comprise one or more nucleotides, a suitable buffer, and/or one or more DNA polymerases. The compositions of the invention may also comprise one or more primers. The reverse transcriptases in these compositions preferably have RNase H activity or are reduced or substantially reduced in RNase H activity, and most preferably are enzymes selected from the group consisting of Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase and Human Immunodeficiency Virus (HIV) reverse transcriptase or other ASLV reverse transcriptases. Two subunit RTs are preferred in the use of the invention and such enzymes may contain various forms and combinations of such subunits such as αβ, αα, ββ, etc. and mutants, variants or derivatives thereof. In preferred compositions, the reverse transcriptases are present at working concentrations.

The invention is also directed to methods for making one or more labeled nucleic acid molecules, comprising mixing one or more nucleic acid templates (preferably one or more RNA templates and most preferably one or more messenger RNA templates) with one or more polypeptides or enzymes having reverse transcriptase activity (preferably one or more multi-subunit RTs) and incubating the mixture under conditions sufficient to synthesize one or more first nucleic acid molecules complementary to all or a portion of the one or more nucleic acid templates, wherein said at least one of said synthesized molecules are labeled and/or comprise one or more labeled nucleotides. In a preferred embodiment, the one or more first nucleic acid molecules are single-stranded cDNA molecules. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a labeled cDNA library, in accordance with the invention. Preferred cellular sources of nucleic acid templates include bacterial cells, fungal cells, plant cells and animal cells.

The invention also concerns methods for making one or more double-stranded nucleic acid molecules. Such methods comprise (a) mixing one or more nucleic acid templates (preferably RNA or mRNA, and more preferably a population of mRNA templates) with one or more polypeptides of the invention having reverse transcriptase activity (preferably one or more multi-subunit RTs); (b) incubating the mixture under conditions sufficient to make one or more first nucleic acid molecules complementary to all or a portion of the one or more templates; and (c) incubating the one or more first nucleic acid molecules under conditions sufficient to make one or more second nucleic acid molecules complementary to all or a portion of the one or more first nucleic acid molecules, thereby forming one or more double-stranded nucleic acid molecules comprising the first and second nucleic acid molecules. In accordance with the invention, the first and/or second nucleic acid molecules are labeled (e.g., may comprise one or more of the same or different labeled nucleotides). Thus, labeled nucleotides may be used at one or both synthesis steps. Such methods may include the use of one or more DNA polymerases as part of the process of making the one or more double-stranded nucleic acid molecules. The invention also concerns compositions useful for making such double-stranded nucleic acid molecules. Such compositions comprise one or more reverse transcriptases of the invention and optionally one or more DNA polymerases, a suitable buffer and/or one or more nucleotides (preferably including labeled nucleotides).

The invention is also directed to labeled nucleic acid molecules (particularly single- or double-stranded cDNA molecules) produced according to the above-described methods and to kits comprising these nucleic acid molecules. Such molecules or kits may be used to detect nucleic acid molecules (for example by hybridization) or for diagnostic purposes.

The invention is also directed to kits for use in the methods of the invention. Such kits can be used for making labeled nucleic acid molecules (single- or double-stranded). The kits of the invention comprise a carrier, such as a box or carton, having in close confinement therein one or more containers, such as vials, tubes, bottles and the like. In the kits of the invention, a first container contains one or more of the reverse transcriptase enzymes of the invention (preferably one or more such multi-subunit enzymes such as heterodimer enzymes or two subunit enzymes or variants, derivatives or mutants thereof) or one or more of the compositions of the invention. The kits of the invention may also comprise, in the same or different containers, at least one component selected from one or more DNA polymerases (preferably thermostable DNA polymerases), a suitable buffer for nucleic acid synthesis and one or more nucleotides. Alternatively, the components of the kit may be divided into separate containers. In one aspect, the kits of the invention comprise reverse transcriptases which have RNase H activity or are reduced or substantially reduced in RNase H activity. Such RTs preferably are selected from the group consisting of RSV reverse transcriptase, AMV reverse transcriptase, RAV reverse transcriptase, MAV reverse transcriptase and HIV reverse transcriptase. In additional preferred kits of the invention, the enzymes (reverse transcriptases and/or DNA polymerases) in the containers are present at working concentrations.

Other preferred embodiments of the present invention will be apparent to one of ordinary skill in light of the following description of the invention, and of the claims.

DETAILED DESCRIPTION OF THE INVENTION

Definitions

In the description that follows, a number of terms used in recombinant DNA technology are utilized extensively. In order to provide a clear and more consistent understanding of the specification and claims, including the scope to be given such terms, the following definitions are provided.

Primer. As used herein, "primer" refers to a single-stranded oligonucleotide that is extended by covalent bonding of nucleotide monomers during amplification or polymerization of a nucleic acid molecule.

Template. The term "template" as used herein refers to double-stranded or single-stranded nucleic acid molecules which are to be amplified, synthesized or sequenced. In the case of a double-stranded molecules, denaturation of its strands to form a first and a second strand is preferably performed before these molecules may be amplified, synthesized or sequenced, or the double-stranded molecule may be used directly as a template. For single stranded templates, at least one primer, complementary to a portion of the template is hybridized under appropriate conditions and one or more polymerases or reverse transcriptases may then synthesize a nucleic acid molecule complementary to all or a portion of said template. The newly synthesized molecules, according to the invention, may be equal or shorter in length than the original template.

Incorporating. The term "incorporating" as used herein means becoming a part of a DNA and/or RNA molecule or primer.

Nucleotide. As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluroescently labeled nucleotides include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham Arlington Heights, Ill.; Fluorescein-15-dATP, Fluorescein-12-dUTP, tetramethyl-rhodamine-6-dUTP, IR$_{770}$-9-dATP, Fluorescein-12-ddUTP, Fluorescein-12-UTP, and Fluorescein-15-2'-dATP available from Boehringer Mannheim Indianapolis, Ind.; and ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

Oligonucleotide. "Oligonucleotide" refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

Hybridization. The terms "hybridization" and "hybridizing" refers to base pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Probes. The term probes refer to single or double stranded nucleic acid molecules or oligonucleotides which are detectably labeled by one or more detectable markers or labels.

Such labels or markers may be the same or different and may include radioactive labels, fluorescent labels, chemiluminescent labels, bioluminescent labels and enzyme labels, although one or more fluorescent labels (which are the same or different) are preferred in accordance with the invention. Probes have specific utility in the detection of nucleic acid molecules by hybridization and thus may be used in diagnostic assays.

Overview

The present invention provides kits, compositions and methods useful in overcoming the labeling limitations often observed during reverse transcription of nucleic acid molecules. Thus, the invention facilitates the production of labeled nucleic acid molecules (particularly cDNA molecules) not heretofore possible.

In general, the invention provides compositions for use in reverse transcription of a nucleic acid molecule to produce labeled nucleic acid molecules. Such compositions may comprise one or more reverse transcriptases (preferably one or more multi-subunit RTs). The enzymes in these compositions are preferably present in working concentrations and have RNase H activity or are reduced or substantially reduced in RNase H activity, although mixtures of enzymes, some having RNase H activity and some reduced or substantially reduced in RNase H activity, may be used in the compositions of the invention. Preferred reverse transcriptases include RSV reverse transcriptase, AMV reverse transcriptase, RAV reverse transcriptase, MAV reverse transcriptase and HIV reverse transcriptase or other ASLV reverse transcriptases.

The invention is also directed to methods for reverse transcription of one or more nucleic acid molecules comprising mixing one or more nucleic acid templates, which is preferably RNA or messenger RNA (mRNA) and more preferably a population of mRNA molecules, with one or more polypeptides having reverse transcriptase activity (preferably multi-subunit RTs) and incubating the mixture under conditions sufficient to make one or more labeled nucleic acid molecules complementary to all or a portion of the one or more templates. To make the nucleic acid molecule or molecules complementary to the one or more templates, at least one primer (e.g., an oligo(dT) primer) and one or more nucleotides (a portion of which are preferably labeled, most preferably fluorescently labeled) are used for nucleic acid synthesis in the 3' to 5' direction. Nucleic acid templates suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Such nucleic acid molecules may also be isolated from viruses.

The invention also provides labeled nucleic acid molecules produced according to the above-described methods. Such labeled nucleic acid molecules may be single or double stranded and are useful as detection probes. Depending on the labeled nucleotide(s) used during synthesis, the labeled molecules may contain one or a number of labels. Where multiple labels are used, the molecules may comprise a number of the same or different labels. Thus, one type or multiple different labeled nucleotides may be used during synthesis of nucleic acid molecules to provide for the labeled nucleic acid molecules of the invention. Such labeled nucleic acid molecules will thus comprise one or more labeled nucleotides (which may be the same or different).

The invention also provides kits for use in accordance with the invention. Such kits comprise a carrier means, such as a box or carton, having in close confinement therein one or more container means, such as vials, tubes, bottles and the like, wherein the kit comprises, in the same or different containers, one or more reverse transcriptases. The kits of the invention may also comprise, in the same or different containers, one or more DNA polymerases, one or more primers, one or more suitable buffers and/or one or more nucleotides (such as deoxynucleoside triphosphates (dNTPs) and preferably fluorescently labeled dNTP's).

In a preferred aspect, the RTs used in the invention comprise two or more subunits (or derivatives, variants, fragments or mutants thereof) and preferably comprise two subunits (e.g., a dimer or heterodimer). Two subunit reverse transcriptases typically have an $\alpha$ and $\alpha\beta$ subunit forming a dimer, although any form or combination of subunits (and derivatives, variants or mutants of such subunits) may be used. Such combinations may include $\alpha\beta$, $\beta\beta$, $\alpha\alpha$ and the like. Preferred two subunit RTs for use in the invention include HIV RT, RSV RT, AMV RT, AEV RT, RAV RT, HIV RT and MAV RT, or other ASLV RTs, or mutants, variants or derivatives thereof. In a preferred aspect, AMV RT and/or RSV RT is used in accordance with the invention. Reverse transcriptases for use in the invention may be obtained from natural or recombinant sources. See, for example, published PCT application WO 98/47912. Alternatively, reverse transcriptases for use in the invention may be obtained commercially, or example, from Life Technologies, Inc. (Rockville, Md.), Pharmacia (Piscataway, N.J.), Sigma (St. Louis, Mo.), or Boehringer Mannheim Biochemicals (Indianapolis, Ind.). In a related aspect, at least one subunit of the RTs of the invention may be modified or mutated to affect the activity of the enzyme such as to reduce, substantially reduce or eliminate RNase H activity. Preferred RTs for use in the invention including ThermoScript™ and ThermoScript™ II obtainable from Life Technologies, Inc. and others described in WO 98/47912 which is incorporated by reference in its entirety.

In accordance with the invention, the amount of labeled product is preferably measured based on percent incorporation of the label of interest into synthesized product as may be determined by one skilled in the art and as discussed in the Examples, although other means of measuring the amount or efficiency of labeling of product will be recognized by one of ordinary skill in the art. The invention provides for enhanced or increased percent incorporation of labeled nucleotide during synthesis of a nucleic acid molecule from a template, preferably during synthesis of one or more cDNA molecules from RNA. According to the invention, such enhancement or increase in percent incorporation is preferably about equal to or greater than a 2-fold, a 5-fold, a 10-fold, a 15-fold, a 20-fold, a 25-fold, a 30-fold, a 40-fold or a 50-fold increase or enhancement in percent incorporation compared to a standard reverse transcriptase such as MMLV RT and preferably SuperScript™ or SuperScript™ II available from Life Technologies, Inc. In another aspect, the percent incorporation of the labeled nucleotide (preferably a fluorescent nucleotide) during synthesis is equal to or greater than about 5%, equal to or greater than about 7.5%, equal to or greater than about 10%, equal to or greater than about 15%, equal to or greater than about 20%, equal to or greater than about 25% equal to or greater than about 30%, equal to or great than about 40% or equal to or greater than about 50%.

Enzymes for use in the invention may include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. See generally U.S. Pat. No. 5,668,005 and published PCT application WO 98/47912. By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wildtype or RNase H+ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), and in U.S. Pat. No. 5,668,005, the disclosures of all of which are fully incorporated herein by reference.

Preferred enzymes for use in the invention include, but are not limited to, RSV H− reverse transcriptase, AMV H− reverse transcriptase, RAV H− reverse transcriptase, MAV H− reverse transcriptase and HIV H− reverse transcriptase (see generally WO 98/47912). Particularly preferred enzymes used in the invention include ThermoScript™ and ThermoScript™ II obtainable from Life Technologies, Inc. It will be understood by one of ordinary skill, however, that any enzyme capable of producing a DNA molecule from a ribonucleic acid molecule (i.e., having reverse transcriptase activity) that is substantially reduced in RNase H activity may be equivalently used in the compositions, methods and kits of the invention.

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Pyrococcus furiosis* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, Thermusflavus (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, Mycobacterium spp. DNA polymerase (Mtb, Mlep), and mutants, variants and derivatives thereof.

DNA polymerases used in accordance with the invention may be any enzyme that can synthesize a DNA molecule from a nucleic acid template, typically in the 5' to 3' direction. Such polymerases may be mesophilic or thermophilic, but are preferably thermophilic. Mesophilic polymerases include T5 DNA polymerase, T7 DNA polymerase (Wiemann, S., et al., *BioTechnique* 18:688 (1995) and Voss, H., et al., *BioTechnique* 23:312 (1997)), Klenow fragment DNA polymerase, DNA polymerase III, and the like. Preferred DNA polymerases are thermostable DNA polymerases such as Taq (Voss, H., et al., *BioTechnique* 23:312 (1997)), Tne, Tma, Pfu, VENT™, DEEPVENT™, Tth (Chang, H., et al., *J Immuno. Methods* 176:235 (1994)) and mutants, variants and derivatives thereof (U.S. Pat. Nos. 5,436,149; 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M., et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. Nos. 5,436,149; 5,512,462; and Barnes, W. M., *Gene* 112:29–35 (1992), the disclosures of all of which are incorporated herein in their entireties.

Formulation of Enzyme Compositions

To form the compositions of the present invention, one or more reverse transcriptases are preferably admixed in a buffered salt solution. One or more DNA polymerases and/or one or more nucleotides (preferably including one or more fluorescent nucleotides which may be the same or different) may optionally be added to make the compositions of the invention. The compositions of the invention may also comprise one or more nucleic acid templates and/or one or more primers. More preferably, the enzymes are provided at working concentrations in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about −20° C., and about six months or longer at a temperature of about −80° C. As used herein, the term "working concentration" means the concentration of an enzyme that is at or near the optimal concentration used in a solution to perform a particular function (such as reverse transcription of nucleic acids).

The water used in forming the compositions of the present invention is preferably distilled, deionized and sterile filtered (through a 0.1–0.2 micrometer filter), and is free of contamination by DNase and RNase enzymes. Such water is available commercially, for example from Sigma Chemical Company (Saint Louis, Mo.), or may be made as needed according to methods well known to those skilled in the art.

In addition to the enzyme components, the present compositions preferably comprise one or more buffers and cofactors necessary for synthesis of a labeled nucleic acid molecule such as a cDNA molecule. Particularly preferred buffers for use in forming the present compositions are the acetate, sulfate, hydrochloride, phosphate or free acid forms of Tris-(hydroxymethy)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions. Addition of one or more carbohydrates and/or sugars to the compositions and/or synthesis reaction mixtures may also be advantageous, to support enhanced stability of the compositions and/or reaction mixtures upon storage. Preferred such carbohydrates or sugars for inclusion in the compositions and/or synthesis reaction mixtures of the invention include, but are not limited to, sucrose, trehalose, and the like. Furthermore, such carbohydrates and/or sugars may be added to the storage buffers for the enzymes used in the production of the enzyme compositions and kits of the invention. Such carbohydrates and/or sugars are commercially available from a number of sources, including Sigma (St. Louis, Mo.).

It is often preferable to first dissolve the buffer salts, cofactor salts and carbohydrates or sugars at working concentrations in water and to adjust the pH of the solution prior to addition of the enzymes. In this way, pH-sensitive enzymes will be less subject to acid- or alkaline-mediated inactivation during formulation of the present compositions.

Concentrations of the RTs in the compositions of the invention may vary depending on th type of reverse transcriptase used. For example, AMV RTs, MAV RTs, RSV RTs and RAV RTs are preferably added at a working concentration in the solution of about 100 to about 5000 units per milliliter, about 125 to about 4000 units per milliliter, about 150 to about 3000 units per milliliter, about 200 to about 2500 units per milliliter, about 225 to about 2000 units per milliliter, and most preferably at a working concentration of about 250 to about 1000 units per milliliter. The enzymes in the thermophilic DNA polymerase group and mutants, variants and derivatives thereof are preferably added at a working concentration in the solution of about 100 to about 1000 units per milliliter, about 125 to about 750 units per milliliter, about 150 to about 700 units per milliliter, about 200 to about 650 units per milliliter, about 225 to about 550 units per milliliter, and most preferably at a working concentration of about 250 to about 500 units per milliliter. The enzymes may be added to the solution in any order, or may be added simultaneously.

The compositions of the invention may further comprise one or more nucleotides (preferably a portion of which are fluorescent nucleotides), which are preferably deoxynucleoside triphosphates (dNTPs). The dNTP components of the present compositions serve as the "building blocks" for newly synthesized nucleic acids, being incorporated therein by the action of the polymerases or reverse transcriptases.

Production of Nucleic Acid or cDNA Molecules

In accordance with the invention, nucleic acid or cDNA molecules (single-stranded or double-stranded) may be prepared from a variety of nucleic acid template molecules. Preferred templates for use in the present invention include single-stranded or double-stranded DNA and RNA molecules, as well as double-stranded DNA:RNA hybrids. More preferred templates include messenger RNA (mRNA), transfer RNA (tRNA) and ribosomal RNA (rRNA) molecules, although mRNA molecules are the preferred template according to the invention.

Preferably the nucleic acid templates may be obtained from natural sources, such as a variety of cells, tissues, organs or organisms. Cells that may be used as sources of nucleic acid molecules may be prokaryotic (bacterial cells, including but not limited to those of species of the genera Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas and Streptomyces) or eukaryotic (including fungi (especially yeasts), plants, protozoans and other parasites, and animals including insects (particularly Drosophila spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid templates (such as mRNA) may be isolated therefrom by methods that are well-known in the art (See, e.g., Maniatis, T., et al, *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be used to prepare cDNA molecules and cDNA libraries in accordance with the present invention.

In the practice of the invention, labeled cDNA molecules or labeled cDNA libraries are produced by mixing one or more nucleic acid molecules obtained as described above, which is preferably one or more mRNA molecules such as a population of mRNA molecules, with one or more polypeptides having reverse transcriptase activity of the invention, or with one or more of the compositions of the invention and preferably with one or more of the RSV RTs and/or AMV RTs and/or other ASLV RTs of the invention, under conditions favoring the reverse transcription of the nucleic acid molecule by the action of the enzymes or the compositions to form one or more labeled cDNA molecule (single-stranded or double-stranded). Thus, the method of the invention comprises (a) mixing one or more nucleic acid templates (preferably one or more RNA or mRNA templates, such as a population of mRNA molecules) with one or more reverse transcriptases of the invention and (b) incubating the mixture under conditions sufficient to make one or more labeled nucleic acid molecules complementary to all or a portion of the one or more templates. The invention may be used in conjunction with methods of cDNA synthesis such as those described in the Examples below, or others that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Labora-* tory Manual, 2nd ed., Cold Spring Harbor, N.Y.: Cold Spring Harbor Laboratory Press, pp. 8.60–8.63 (1989)), to produce cDNA molecules or libraries.

In other aspects, the invention may be used in methods for amplifying nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more polypeptides having reverse transcriptase activity of the invention and with one or more DNA polymerases and (b) incubating the mixture under conditions sufficient to amplify a labeled nucleic acid molecule complementary to all or a portion of the template. Alternatively, amplification may be accomplished by mixing a template with one or more polypeptides having reverse transcriptase activity of the invention. Incubating such a reaction mixture under appropriate conditions allows amplification of a labeled nucleic acid molecule complementary to all or a portion of the template. Such amplification may be accomplished by the reverse transcriptase activity alone or in combination with a DNA polymerase. Two-step RT-PCR reactions may be accomplished in two separate steps. Such a method comprises (a) mixing a nucleic acid template (e.g., mRNA) with one or more reverse transcriptases of the invention, (b) incubating the mixture under conditions sufficient to make a labeled nucleic acid molecule (e.g., a DNA molecule) complementary to all or a portion of the template, (c) mixing the labeled nucleic acid molecule with one or more DNA polymerases and (d) incubating the mixture of step (c) under conditions sufficient to amplify the labeled nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822).

Kits

In another embodiment, the present invention may be assembled into kits for use in reverse transcription or amplification of a nucleic acid molecule. Kits according to this aspect of the invention comprise a carrier means, such as a box, carton, tube or the like, having in close confinement therein one or more container means, such as vials, tubes, ampules, bottles and the like, wherein a first container means contains one or more polypeptides of the invention having reverse transcriptase activity. The kits of the invention may also comprise (in the same or separate containers) one or more DNA polymerases, a suitable buffer, one or more nucleotides (preferably including one or more fluorescent nucleotides which may be the same or different) and/or one or more primers.

In a specific aspect of the invention, the reverse transcription and amplification kits may comprise one or more components (in mixtures or separately) including one or more polypeptides having reverse transcriptase activity of the invention, one or more nucleotides needed for synthesis of a labeled nucleic acid molecule, and/or one or more primers (e.g., oligo(dT) for reverse transcription). Such reverse transcription and amplification kits may further comprise one or more DNA polymerases. Preferred polypeptides having reverse transcriptase activity, DNA polymerases, nucleotides, primers and other components suitable for use in the reverse transcription and amplification kits of the invention include those described herein. The kits encompassed by this aspect of the present invention may further comprise additional reagents and compounds necessary for carrying out standard nucleic acid reverse transcription or amplification protocols. Such kits may also comprise instructions for labeling nucleic acid molecules in accordance with the invention.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

First Strand cDNA Synthesis Using Fluorescent Nucleotide

For the SuperScript™ II reactions, Cy3-dUTP or R110-dUTP was incorporated into cDNA using 1 µg of Hela mRNA, primed with 1 µg of oligo d(T) 25 mer. But for the AMV RT and ThermoScript™ reactions, 0.5 µg of oligo d(T) 25 mer was used to prime 1 µg Hela mRNA. This mixture was heated to 70° C. for 10 min, and then transferred to ice for 10 min. The reaction conditions varied between the reverse transcriptases. The SuperScript II™ reaction buffer contained 50 mM Tris-HCl (pH 8.3), 75 mM KCl, 3 mM MgCl$_2$, 10 mM DTT, 1 µCi P$^{32}$ α-dCTP, 500 µM dNTPs, and 100 µM fluorescent dUTP. The ThermoScript™ reaction buffer contained 50 mM Tris-HCl (pH 8.4), 75 mM KCl, 7.5 mM MgCl$_2$, 10 mM DTT, 2 µCi P$^{32}$ α-dCTP, 1 mM dNTPs, and 200 µM fluorescent dUTP. The AMV RT reaction buffer contained 100 mM Tris-HCl (pH 8.3), 100 mM KCl, 10 mM MgCl$_2$, 10 mM DTT, 0.5 µCi P$^{32}$ α-dCTP, 250 µM dNTPs, and 100 µM fluorescent dUTP. The reaction buffer was added to the Hela mRNA and oligo d(T) 25 mer mixture. Two hundred units of SuperScript II™, 15 units of ThermoScript™, or 7.5 units of AMV RT was used in the reaction. Then the reaction was incubated at the RT's optimal reaction temperature (45° C. for SuperScript™ II, 55° C. for ThermoScript™ and 42° C. for AMV RT) for one hour. Two microliters of the reaction mixture was pippeted and mixed with 5 µg of yeast tRNA in a final of 50 µl of 20 mM EDTA solution. This EDTA solution was used in the first strand cDNA yield calculation.

TCA Precipitation and First Strand cDNA Synthesis Yield Calculation

Duplicate 10 µl samples (from 20 mM EDTA solution) were spotted onto glass fiber filters and dried under a heat lamp for 15 min. One set of the filters was washed once with ice-cold 10% (w/v) TCA solution and twice with 5% TCA solution (10 min. perwash) at room temperature. After the washes, the filters were washed with 95% ethanol for 5 min. and then dried under a heat lamp. The washed and unwashed filters were counted in standard scintillant to determine the amount of P$^{32}$ in the reaction, as well as the amount of P$^{32}$ that was incorporated. The equation used for the calculation of first strand synthesis yield is as follows:

Specific Activity $(SA;\ \text{cpm/pmol dCTP}) =$ $$\frac{\text{cpm of 10 μl from unwashed sample}}{200 \text{ pmol dCTP}}$$

Amount of cDNA (μg) =

$$\frac{\text{cpm of washed sample} \times 50 \times (4 \text{ pmole dNTP/pmole dCTP})}{SA \times (3{,}030 \text{ pmole dNTP/μg cDNA})}$$

Absorbance for Fluorescent Nucleotide Incorporation

Two to four microliters of the first strand reaction mixture was saved, this was used as a "standard", and the remaining 16–18 μl of the first strand reaction mixture was precipitated with one half volume of $NH_4Ac$ and 2.5-fold volume of ethanol, and 5 μg of yeast tRNA as a carrier. Following precipitation, the pellet was washed twice with 70% ethanol to lower background fluorescence. The precipitates were resuspended in 50 mM Tris buffer (pH 7.5), and the fluorescent nucleotide incorporation was determined. The "standard" was diluted in 50 mM Tris buffer and the absorbance determined. The excitation spectra for Cy3-dUTP and R110-dUTP are 550 nm and 503 nm. The emission spectra ranges are 560–600 nm for Cy3-dUTP and 508–560 nm for R110-dUTP. The difference between the "standard" and the ethanol precipitated sample is the fluorescent nucleotide incorporation.

Calculation of Percent Incorporation Sample from SS II, TS I with Cy3-dUTP/Hela mRNA A. Standard Curve, which is a series dilution of standard sample containing 200 μM of Cy3-dUTP.

| Dilution | Light units, peak of emission | Convert concentration, nM |
|---|---|---|
| 1:1,000 | 1,796,330 | 200 |
| 1:2,000 | 822,791 | 100 |
| 1:4,000 | 437,004 | 50 |
| 1:8,000 | 221,297 | 25 |
| 1:16,000 | 114,387 | 12.5 |
| 1:32,000 | 59,297 | 6.25 |
| 1:64,000 | 30,642 | 3.13 |

B. Sample of SS II with Cy3-dUTP/ Hela mRNA

The unprecipitated reaction sample contained 100 p mole/μl of Cy3-dUTP, which calculated from the concentration of 100 μM Cy3-dUTP in 1 μl.

The precipitated reaction sample (total of 14 μl), which contained Cy3-dUTP incorporated cDNA, will be measured in emission (14 μl). The light units will be converted to nM by the standard curve.

14 μl of SS II w/Cy3-dUTP (100 μM in reaction)
=97,347 light units
=13 nM (in 2 ml vol)
The p mole conversion: 13 nM×(2/1000 liter)
=26 p mole (in 14 μl)
=1.86 p mole/μl
1.86/100=1.86% (incorporation)

C. Sample of TS I with Cy3-dUTP/Hela mRNA

The unprecipated reaction sample contained 200 p mole/μl of Cy3-dUTP.

The precipitated reaction sample (2 μl) will be measured in emission.

2 μl of TS I w/Cy3-dUTP (200 μM in reaction)
=282,729 light units
=34 nM (in 2 ml vol)
The p mole conversion: 34 nM×(2/1000 liter)
=68 p mole (in 2 μl)
=34 p mole/μl
34/200=17% (incorporation)

Comparison of SuperScript™ II (SS II) and ThermoScript™ (TS I) in Cy3-dUTP incorporation in 2.3 Kb control RNA and MAP4 RNA (5.0 Kb).

|  | cDNA synthesis Yield (%) | Cy3-dUTP Incorp. (%) | Fluorescent nucleotide incorp. Increased (fold) |
|---|---|---|---|
| SS II & 2.3 Kb RNA | 20.1 | 1.3 | — |
| TS I & 2.3 Kb RNA | 23.0 | 9.4 | 7.2 |
| SS II & MAP4 RNA | 33.0 | 1.2 | — |
| TS I & MAP4 RNA | 38.6 | 18.4 | 15.3 |

Note: The cDNA synthesis yield with normal dNTP are 28.8% for SS II, 33.3% for TS I.

Comparison of SS II, TS I, ThermoScript™ II (TS 2) and AMV RT in Cy3-dUTP and Rh110-dUTP incorporation in HeLa m-RNA.

|  | cDNA Synthesis Yield (%) | Cy3-dUTP Incorp. (%) | Fluorescent nucleotide incorp. Increased (fold) |
|---|---|---|---|
| SS II & HeLa/Cy3dU | 27.9 | 1.86 | — |
| TS I & HeLa/Cy3dU | 21.0 | 17.0 | 9.1 |
| TS II & HeLa/Cy3dU | 21.0 | 19.4 | 10.4 |
| AMV & HeLa/Cy3dU | 20.3 | 20.5 | 11.0 |
| SS II & HeLa/R110dU | 19.8 | 2.57 | — |
| TS I & HeLa/R110dU | 14.9 | 20.67 | 8.0 |
| TS II & HeLa/R110dU | 13.1 | 25.33 | 9.9 |
| AMV & HeLa/R110dU | 10.0 | 24.5 | 9.5 |

Note: The cDNA synthesis yield with normal dNTP are 30.7% for SS II, 26.1% for TS I, 26.9% for TS II, and 22.1% for AMV RT.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition for use in labeling one or more nucleic acid molecules, said composition comprising (a) one or more enzymes having reverse transcriptase activity, wherein said enzymes are multi-subunit enzymes;

(b) one or more labeled nucleotides, with the proviso that said labeled nucleotides are not labeled dideoxynucleotides; and (c) one or more nucleotides without labels.

2. The composition of claim 1, wherein said enzymes are heterodimers.

3. The composition of claim 1, wherein said enzymes are selected from the group consisting of ASLV reverse transcriptases.

4. The composition of claim 1, wherein said enzymes are reduced or substantially reduced in RNase H activity.

5. The composition of claim 1, wherein said enzymes are selected from the group consisting of RSV reverse transcriptase, AMV reverse transcriptase, RAV reverse transcriptase, MAV reverse transcriptase and HIV reverse transcriptase, and fragments or mutants thereof having DNA polymerase activity.

6. The composition of claim 1, wherein said one or more labeled nucleotides are one or more fluorescently labeled nucleotides.

7. The composition of claim 6, wherein said nucleotides are labeled with a fluorescent molecule or marker selected from the group consisting of rhodamine, fluorescein, Cy3 and Cy5.

8. The composition of claim 1, wherein said composition further comprises one or more DNA polymerases, and mutants and fragments thereof having DNA polymerase activity.

9. The composition of claim 1, wherein said composition further comprises a reverse transcription buffer and/or a nucleic acid template.

10. A method for reverse transcription of one or more nucleic acid molecules comprising
    (a) mixing one or more nucleic acid templates with (i) one or more enzymes having reverse transcriptase activity, wherein said enzymes are multi-subunit enzymes, (ii) one or more labeled nucleotides, with the proviso that said labeled nucleotides are not labeled dideoxynucleotides, and (iii) one or more nucleotides without labels; and
    (b) incubating said mixture under conditions sufficient to make one or more nucleic acid molecules complementary to all or a portion of said one or more templates, wherein at least one of said first nucleic acid molecules is detectably labeled.

11. The method of claim 10, wherein said nucleic acid template is a messenger RNA (mRNA) molecule or a population of mRNA molecules.

12. The method of claim 10, said method further comprising incubating said one or more first nucleic acid molecules under conditions sufficient to make one or more second nucleic acid molecules complementary to all or a portion of said one or more first nucleic acid molecules.

13. The method of claim 10, wherein said enzymes are selected from the group consisting of ASLV reverse transcriptases.

14. The method of claim 10, wherein said enzymes are selected from the group consisting of RSV RT, AMV RT, ThermoScript™ and ThermoScript™ II.

15. The method of claim 10, wherein said detectable label is a fluorescent label.

16. The method of claim 15, wherein said fluorescent label is selected from the group consisting of fluorescein, rhodamine, Cy3 and Cy5.

17. The method of claim 10, wherein said detectably labeled first nucleic acid molecules comprise one or more fluorescently labeled nucleotides.

18. The method of claim 10, wherein said detectable labels are the same or different.

19. The method of claim 18, wherein said detectable labels are fluorescent labels.

20. A labeled nucleic acid molecule prepared according to the method of claim 10.

21. A kit for use in labeling one or more nucleic acid molecules, said kit comprising
    (a) one or more enzymes having reverse transcriptase activity, wherein said enzymes are multi-subunit enzymes;
    (b) one or more labeled nucleotides, with the proviso that said labeled nucleotides are not labeled dideoxynucleotides; and
    (c) one or more nucleotides without labels.

22. The kit of claim 21, said kit further comprising one or more components selected from the group consisting of one or more DNA polymerases, a suitable buffer and one or more primers.

23. The kit of claim 22, wherein at least one or said nucleotides are fluorescent nucleotides.

24. The kit of claim 21, wherein said enzymes are heterodimers.

25. The kit of claim 21, wherein said enzymes are selected from the group of ASLV reverse transcriptases.

26. The kit of claim 21, wherein said enzymes are reduced or substantially reduced in RNase H activity.

27. The kit of claim 21, wherein said enzymes are selected from the group consisting of RSV reverse transcriptase, AMV reverse transcriptase, RAV reverse transcriptase, MAV reverse transcriptase and HIV reverse transcriptase, and fragments or mutants thereof having DNA polymerase activity.

28. The kit of claim 23, wherein said nucleotides are labeled with a fluorescent molecule or marker selected from the group consisting of rhodamine, fluorescein, Cy3 and Cy5.

29. A composition for use in labeling one or more nucleic acid molecules, said composition comprising
    (a) one or more enzymes having reverse transcriptase activity, wherein said enzymes are multi-subunit enzymes;
    (b) one or more labeled nucleotides, with the proviso that said labeled nucleotides are not labeled dideoxynucleotides;
    (c) one or more nucleotides without labels; and
    (d) one or more RNA templates.

30. The composition of claim 29, wherein said one or more RNA templates is a messenger RNA (mRNA) molecule or a population of mRNA molecules.

31. The composition of claim 29, wherein said enzymes are heterodimers.

32. The composition of claim 29, wherein said enzymes are selected from the group consisting of ASLV reverse transcriptases.

33. The composition of claim 29, wherein said enzymes are reduced or substantially reduced in RNase H activity.

34. The composition of claim 29, wherein said enzymes are selected from the group consisting of RSV reverse transcriptase, AMV reverse transcriptase, RAV reverse transcriptase, MAV reverse transcriptase and HIV reverse transcriptase, and fragments or mutants thereof having DNA polymerase activity.

35. The composition of claim 29, wherein said one or more labeled nucleotides are one or more fluorescently labeled nucleotides.

36. The composition of claim 35, wherein said nucleotides are labeled with a fluorescent molecule or marker selected from the group consisting of rhodamine, fluorescein, Cy3 and Cy5.

37. The composition of claim 29, wherein said composition further comprises one or more DNA polymerases, and mutants and fragments thereof having DNA polymerase activity.

38. The composition of claim 29, wherein said composition further comprises a reverse transcription buffer.

39. A method for reverse transcription of one or more nucleic acid molecules comprising
   (a) mixing one or more RNA templates with (i) one or more enzymes having reverse transcriptase activity, wherein said enzymes are multi-subunit enzymes, (ii) one or more labeled nucleotides, with the proviso that said labeled nucleotides are not labeled dideoxynucleotides, and (iii) one or more nucleotides without labels; and
   (b) incubating said mixture under conditions sufficient to make one or more nucleic acid molecules complementary to all or a portion of said one or more templates, wherein at least one of said first nucleic acid molecules is detectably labeled.

40. The method of claim 39, wherein said one or more RNA templates is a messenger RNA (mRNA) molecule or a population of mRNA molecules.

41. The method of claim 39, said method further comprising incubating said one or more first nucleic acid molecules under conditions sufficient to make one or more second nucleic acid molecules complementary to all or a portion of said one or more first nucleic acid molecules.

42. The method of claim 39, wherein said enzymes are selected from the group consisting of ASLV reverse transcriptases.

43. The method of claim 39, wherein said enzymes are selected from the group consisting of RSV RT, AMV RT, ThermoScript™ and ThermoScript™ II.

44. The method of claim 39, wherein said detectable label is a fluorescent label.

45. The method of claim 44, wherein said fluorescent label is selected from the group consisting of fluorescein, rhodamine, Cy3 and Cy5.

46. The method of claim 39, wherein said detectably labeled first nucleic acid molecules comprise one or more fluorescently labeled nucleotides.

47. The method of claim 39, wherein said detectable labels are the same or different.

48. The method of claim 47, wherein said detectable labels are fluorescent labels.

49. A labeled nucleic acid molecule prepared according to the method of claim 39.

50. A kit for use in labeling one or more nucleic acid molecules, said kit comprising
   (a) one or more enzymes having reverse transcriptase activity, wherein said enzymes are multi-subunit enzymes;
   (b) one or more labeled nucleotides, with the proviso that said labeled nucleotides are not labeled dideoxynucleotides;
   (c) one or more nucleotides without labels; and
   (d) one or more RNA templates.

51. The kit of claim 50, said kit further comprising one or more components selected from the group consisting of one or more DNA polymerases, a suitable buffer and one or more primers.

52. The kit of claim 50, wherein said enzymes are heterodimers.

53. The kit of claim 50, wherein said enzymes are selected from the group of ASLV reverse transcriptases.

54. The kit of claim 50, wherein said enzymes are reduced or substantially reduced in RNase H activity.

55. The kit of claim 50, wherein said enzymes are selected from the group consisting of RSV reverse transcriptase, AMV reverse transcriptase, RAV reverse transcriptase, MAV reverse transcriptase and HIV reverse transcriptase, and fragments or mutants thereof having DNA polymerase activity.

56. The kit of claim 52, wherein said nucleotides are labeled with a fluorescent molecule or marker selected from the group consisting of rhodamine, fluorescein, Cy3 and Cy5.

57. The kit of claim 50, wherein said one or more RNA templates is a messenger RNA (mRNA) molecule or a population of mRNA molecules.

58. The composition of claim 1, wherein said one or more labeled nucleotides are selected from the group consisting of a ribonucleoside triphosphate, a deoxyribonucleoside triphosphate, dATP, dCTP, dITP, dUTP, dGTP, dTTP, [αS] dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

59. The method of claim 10, wherein said one or more labeled nucleotides are selected from the group consisting of a ribonucleoside triphosphate, a deoxyribonucleoside triphosphate, dATP, dCTP, dITP, dUTP, dGTP, dTTP, [αS] dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

60. The kit of claim 21, wherein said one or more labeled nucleotides are selected from the group consisting of a ribonucleoside triphosphate, a deoxyribonucleoside triphosphate, dATP, dCTP, dITP, dUTP, dGTP, dTTP, [αS] dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL- 14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

61. The composition of claim 29, wherein said one or more labeled nucleotides are selected from the group consisting of a ribonucleoside triphosphate, a deoxyribonucleoside triphosphate, dATP, dCTP, dITP, dUTP, dGTP, dTTP, [αS]dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

62. The method of claim 39, wherein said one or more labeled nucleotides are selected from the group consisting of a ribonucleoside triphosphate, a deoxyribonucleoside triphosphate, dATP, dCTP, dITP, dUTP, dGTP, dTTP, [αS]dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

63. The kit of claim 50, wherein said one or more labeled nucleotides are selected from the group consisting of a ribonucleoside triphosphate, a deoxyribonucleoside triphosphate, dATP, dCTP, dITP, dUTP, dGTP, dTTP, [αS]dATP, 7-deaza-dGTP, 7-deaza-dATP, [R6G]dUTP, [TAMRA]dUTP, [R110]dCTP, [R6G]dCTP, [TAMRA]dCTP, FluoroLink DeoxyNucleotides, FluoroLink Cy3-dCTP, FluoroLink Cy5-dCTP, FluoroLink FluorX-dCTP, FluoroLink Cy3-dUTP, FluoroLink Cy5-dUTP, Fluorescein-15-dATP, Fluorescein-12-dUTP, tetramethyl-rhodamine-6-dUTP, $IR_{770}$-9-dATP, Fluorescein-12-UTP, Fluorescein-15-2'-dATP, ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP.

* * * * *